United States Patent [19]

Gaffar et al.

[11] Patent Number: 4,826,675

[45] Date of Patent: May 2, 1989

[54] ANTICALCULUS ORAL COMPOSITION

[75] Inventors: Abdul Gaffar, Princeton; Shek-Hong Lau, Dayton; John Afflitto, Brookside, all of N.J.

[73] Assignee: Colgate-Palmolive Company, New York, N.Y.

[21] Appl. No.: 157,210

[22] Filed: Feb. 17, 1988

[51] Int. Cl.$^4$ .......................... A61K 7/16; A61K 7/18
[52] U.S. Cl. ........................................ 424/52; 424/49
[58] Field of Search ........................................ 424/52

[56] References Cited

U.S. PATENT DOCUMENTS

| | | | |
|---|---|---|---|
| 3,934,002 | 1/1976 | Haefele | 424/54 |
| 4,259,316 | 3/1981 | Nakashima et al. | 424/52 |
| 4,263,276 | 4/1981 | Harvey | 424/52 |
| 4,305,928 | 12/1981 | Harvey | 424/52 |
| 4,335,102 | 6/1982 | Nakashima et al. | 424/52 |
| 4,528,181 | 7/1985 | Morton et al. | 424/52 |

Primary Examiner—Shep K. Rose
Attorney, Agent, or Firm—Robert L. Stone; Murray M. Grill

[57] ABSTRACT

An Anticalculus Oral Composition, typically a mouthwash or dentifrice gel, containing compound having C-O-P bonds, such as phytic acid or an alkali metal (including ammonium) salt thereof as anticalculus agent, homogeneously distributed in a dentally acceptable oral vehicle. Also, present to inhibit enzymatic hydrolysis of the phytic compound and to promote caries reduction is an alkali metal fluoride.

9 Claims, No Drawings

ANTICALCULUS ORAL COMPOSITION

This invention relates to oral compositions containing an anticalculus agent.

Calculus is a hard, mineralized deposit which forms on the teeth. Regular brushing aids in preventing a rapid buildup of such deposit, but even regular brushing is not sufficient to remove the calculus which adheres to the teeth. Calculus is formed on the teeth when cyrstals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline HAP is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including HAP. It is apparent therefore that agents which effectively interfere with crystalline growth of HAP will be effective as anticalculus agents. A suggested mechanism by which the anticalculus agents of this invention inhibit calculus formation probably involves an increase of the activation energy barrier thus inhibiting the transformation of precursor amorphous calcium phosphate to HAP.

Studies have shown that there is a good correlation between the ability of a compound to prevent HAP crystalline growth in vitro and its ability to prevent calcification in vivo, provided of course that such compound is stable in and inert to saliva and its components.

Compounds containing P—O—P bonds have been used to inhibit HAP formation in vitro. They include the structure:

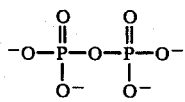

However, as described in U.S. Pat. No. 4,627,977 to Gaffar, et al, (Colgate-Palmolive Co.) such compounds are hydrolyzed in the oral cavity by various phosphatases and can have reduced efficacy with respect to their inhibitory effect on HAP formation. A combination of fluoride ion in the presence of polycarboxylate is required to inhibit the hydrolysis of P—O—P bonds.

Compounds containing C—O—P bonds, particularly 6 C—O—P bonds, such as phytic acid, that is , myo-inositol 1,2,3,4,5,6- hexakis (dihydrogen phosphate), having the structure

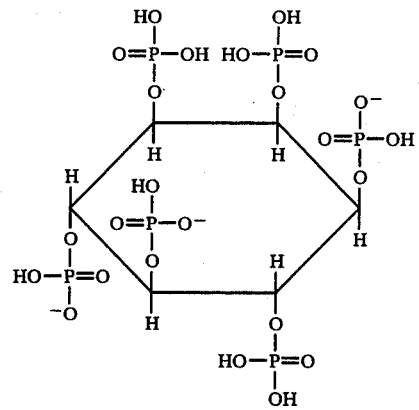

have been recommended for various purposes in oral compositions. However, effective inhibition of HAP formation with compositions including such compounds containing C—O—P bonds have not been known beyond such recommendation or speculation.

PRIOR ART BACKGROUND

Kaufman & Kleinberg, IADR Abstracts, 1973, No. 444, Page 169, titled "X-Ray Diffraction Study of the Effect of Phytate on the In Vitro Formation of Calcium Phosphate", tested the effect of phytate on the crystallization of calcium phosphate salts and concluded that phytate can inhibit apatite crystallization. The authors commented that this inhibition may suit phytate for preventing formation of dental calculus. This disclosure, however, was based on in vitro conditions and did not take into account in vivo enzymatic hydrolysis. For instance, both fluoride and polycarboxylate are required to provide sufficient inhibition of enzymatic hydrolysis when compounds containing P—O—P bonds are employed against calculus formation, as described in U.S. Pat. No. 4,627,977.

Oral anticaries compositions containing phytate compound and a stannous compound are known, for instance in U.S. Pat. Nos. 4,259,316 and 4,335,102, each to Nakashima et al(Lion Corp.), as well as in Japanese Patent Application Disclosures Nos. 56 095112(1981); 56 075422(1981); 56 045408(1981): 56 039008(1981); and 56 022721(1981); each to Lion Corp. Due to complex formation between polyvalent cations and phytate anion, the presence of stannous compound in an oral composition containing a phytate compound would not be desirable for inhibition of calculus formation.

In U.S. Pat. No. 3,934,002 to Haefele (Proctor & Gamble Co.). Phytic acid is disclosed as one of the anticalculus compounds in oral compositions used together with bis-biguanide antiplaque and anticaries agent. These agents react with one another so that the anticalculus agent would not be homogeneously distributed throughout the oral compositions. Indeed, since both agents are present, if a mouthrinse is prepared, it contains two visibly distinct phases, one being solid phase reaction product of bis-biguanide and anticalculus agent is present. Moreover, if a dentifrice is prepared, it is suggested to avoid an abrasive or polishing agent which adsorbs bis-biguanide compound. Siliceous polishing agents are generally recognized by those knowledgeable in the art as being incompatible with bis-biguanides due to such adsorption. Japanese Patent Application Disclosure No. 61 200905(1986) also describes oral compositions containing chlorhexidine, a bis-biguanide, and phytic acid.

In U.S. Pat. No. 4,193,988 to Forward et al. (Beecham Group Ltd) anticaries oral hygiene compositions are taught containing sodium monofluorophosphate and calcium glycerophosphate wherein calcium phytate may also be present.

In U.S. Pat. No. 4,332,791 to Raaf et al (Blendax-W. Rice), toothpaste is described containing copper compound, one of which may be copper phytate.

In U.S. Pat. Nos. 4,263,270 and 4,305,928, each to Harvey (Colgate-Palmolive Co.) dentifrice containing siliceous polishing agent is described wherein phytic acid prevents color fading when alkali metal monofluorophosphate is present. In an aspect of the inventions described in these patents sodium fluoride may be employed. However, when it is, phytic acid is not used.

In U.S. Pat. No. 4,528,181 to Morton et al (Colgate-Palmolive Co.), phytate is taught to improve fluoride retention in a dentifrice containing a dual source of fluoride (sodium fluoride and sodium monofluorophosphate and a synthetic, precipitated, amorphous silica gel polishing agent. Thus, this patent requires the presence of monofluorophosphate together with phytate.

Belgian Pat. No. 903,498 to Siren provides a detailed disclosure of many inositol triphosphates and includes a brief mention of proposed utilities including possible use as additive in a dentifrice paste. No potential is indicated for HAP inhibition.

Japanese Patent Application Disclosure No. A62 000418(1987) to Lion Corp., Discloses an oral hygiene composition containing hydroxamic acid, a polyphosphoric acid, such as phytic acid, and monofluorophosphoric acid.

In Japanese Patent application Disclosure No. 61 036211(1986) to Lion Corp., sodium and ammonium phytates are disclosed as alternatives to polyphosphates which contain P—O—P bonds, in combination with a compound of a polyvalent metal, particularly magnesium, barium or strontium. Although, it is indicated that the dental composition is intended to reduce calculus formation, the composition admits of complex formation due to the presence of polyvalent metal.

Phytic acid and its derivatives are also described in dentifrices intended to remove dental nicotine stains in Japanese Patent Application Disclosures Nos. 56 018913(1981) describing a dental cleanser and 56 018911(1981), describing a toothpaste, each to Lion Corp. Fluoride is not disclosed, moreover, in the toothpaste of 56 018911, which contains polyvalent cation salt as polishing material.

A tartar preventing chewing gum containing phytate salt is described in Japanese Published Application No. 61 233612(1986) to Kao Corp. Since soluble contents of chewing gums are intended for ingestion fluoride-providing materials are generally to be avoided in chewing gums. They are not disclosed in this patent publication.

SUMMARY OF THE INVENTION

It is an object of this invention to provide an improved anti-calculus Oral Composition which will not be subject to diminished effectiveness in inhibiting HAP formation due to enzymatic hydrolysis.

A further object of this invention is to provide an anticalculus oral composition in which a phytic compound anticalculus agent is homogeneously distributed in the oral composition.

A further object of this invention is to promote reduction is caries by the anticalculus oral composition.

Other advantages and objects will appear in the following description.

DETAILED DESCRIPTION OF THE INVENTION

In accordance with certain of its aspects, this invention relates to an anticalculus oral composition consisting essentially of a dentally acceptable oral vehicle and homogeneously distributed therein about 0.1-7% by weight of a compound having C—O—P bonds selected from the group consisting of phytic acid, myo-inositol tetrakis (dihydrogen phosphate), myo-inositol trikis dihydrogen phosphate, phosphoglyceric acid, phosphoenol pyruvic acid and alkali metal salt thereof as inhibitor of hydroxyapatite formation and about 0.02-2.2% by weight of an alkali metal fluoride as inhibitor of enzymatic hydrolysis and also anticaries agent, said alkali metal fluoride being the sole anticaries agent which provides fluoride to the oral composition, said oral composition containing no compounds which provide polyvalent cations capable of forming a complex with said inhibitor of hydroxyapatite formation.

Phytic acid, also known as myo-inositol 1,2,3,4,5,6-hexakis (dihydrogen phosphate) and inositol hexaphosphoric acid, and its alkali metal (e.g. sodium, potassium as well as ammonium) salts is the preferred compound—containing C—O—P bonds. It, or other indicated compound having C—O—P bonds, is present in the oral composition of the present invention, in amount of about 0.1-7% by weight, as agent which inhibits HAP or calculus formation. When the oral composition is essentially liquid in nature, such as when it is a mouthwash, the phytic acid or salt is typically present in amount of about 0.1-3% by weight preferably about 1-3%; and when it is gel-like in consistency, such as when it is a dentifrice gel, which may be visually clear, hazy or opacified, it is typically present in amount of about 3-7% by weight, preferably about 3-6%.

In order to permit the compound having C—O—P bonds to exert its inhibitory effect on HAP formation, an alkali metal fluoride is present to inhibit enzymatic hydrolysis of the C—O—P compound, particularly under in vivo conditions. The enzymatic inhibitor is particularly effective with a simple fluoride of the alkali metal fluoride type, typically sodium fluoride, potassium fluoride or ammonium fluoride. Such fluoride compounds provide fluoride without complication due to the presence of complex fluorine-containing, e.g. fluorozirconate or fluorophosphate, and do not contain polyvalent cation, e.g. tin, copper or zinc, which would readily form a complex with the phytic compound. Moreover, effective enzymatic inhibition is readily effected when the alkali metal fluoride is present in an effective non-toxic amount, i.e. about 0.02-2.2% by weight of the oral composition, to reduce caries formation. Such amount is typically about 0.02-1% by weight, preferably about 0.02-0.1% in a liquid oral composition such as a mouthwash and typically about 0.1-2.2% by weight preferably about 0.15-0.3% by weight, when the oral composition is gel-like in consistency, such as a dentifrice gel.

In certain highly preferred forms of the invention, the oral composition may be substantially liquid in character, such as a mouthwash or rinse. In such a preparation the vehicle wherein the phytic compound is homogeneously distributed is a water-humectant mixture also containing non-toxic alcohol (e.g. ethanol or isopropyl alcohol). Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight, preferably about 70–96.5% of the preparation. Typically, humectant is present in amount of about 5–30% by weight. Typical humectants employed are glycerine, sorbitol, propylene glycol, polypropylene glycol and/or polyethylene glycol (e.g. 400–600).

The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate etc.).

In certain other desirable forms of this invention, the oral composition may be substantially gel-like or paste-like in a dentifrice gel. The vehicle of such solid oral preparations in which the C—O—P compound is homogeneously distributed contains a liquid moiety of water and humectant and solid moiety of gelling agent together with a siliceous polishing agent having an emperical $SiO_2$ content of at least 70%, a particle size in the range from 1 to 35 microns, preferably from 2 to 20 microns, substantially amorphous X-ray structure and an index of refraction between 1.44 and 1.47.

The proportion of the polishing agent of high silica content is in the range from 5% to 50% of the dentifrice, preferably from 10% to 30% such as from 15% to 25%. One abrasive is an amorphous alkali metal or alkaline earth metal aluminosilicate having a refractive index of from 1.44 to 1.47 and containing at least 70% silica, up to 10% alumina, up to 20% of moisture and up to 10% of sodium oxide. Typically, this material has a particle size in the range from 1 to 35 microns, preferably from 2 to 20 microns, e.g. 2 to 4 microns. The preferred moisture content is from 10% to 20% measured by ignition at 1000° C. and the typical content of sodium oxide is from 5% to 10%. Generally, the polishing agent has a loose bulk density of up to 0.2 g/cc, such as from 0.07 to 0.12 g/cc. Another suitable type of polishing agent is porous amorphous silicic anhydride having an average particle size preferably below 20 microns and above 1 micron, a surface area of at least 200 $m^2/g$, preferably at least 300 $m^2/g$, and a bulk density of at least 0.15 $g/cm^3$ preferably at least 0.30 $g/cm^3$, such as a dehydrated silica hydrogel (i.e. a xerogel), preferably of the well known regular density or intermediate density type. Examples of such amorphous silicic anhydride polishing agents are "Syloid 63", "Syloid 72" and "Syloid 74" (SYLOID is a trade mark) which are described in "The Davison Family of Syloid Silicas" published by their manufacturer, Grace, Division Chemical Company. "Santocel 100" of Monsanto (SANTOCEL is a trade mark), is also a suitable dental abrasive. "Syloid 72"—has an average particle size of about 4 microns, a surface area of about 340 $m^2/g$ and a bulk density of about 1.77 $g/cm^3$. For "Syloid 63" the corresponding figures are about 9 microns, about 675 $m^2/g$ and about 0.4 $g/cm^3$. A grade of "Santocel 100" has a surface area of about 239 $m^2/g$ and a bulk density of about 0.24 $g/cm^3$. These amorphous silicic anhydrides may be used singly or in mixtures.

In the dentifrice, the liquid vehicle may comprise water and humectant typically collectively in an amount ranging from about 10% to about 90% by weight of the preparation. Glycerine, propylene glycol (e.g. 400–600) exemplify suitable humectants. Also advantageous are liquid mixtures of water, glycerine and sorbitol. In clear gels wherein the refractive index is an important consideration, about 3–30% by weight of water, 0 to about 80% by weight of glycerine, and about 20–80% by weight of sorbitol is preferably employed. In hazy or opacified gels, the water content is typically about 10–35% by weight and the humectant about 15–70% by weight.

The dentifrice gel further contains natural or synthetic gelling agent in proportions of about 0.1 to about 10, preferably about 0.5 to about 5g, by weight. Typical gelling agents include Irish moss, gum tragacanth, starch, polyvinylpyrrolidone, hydroxyethylpropylcellulose, hydroxybutyl methyl-cellulose, hydroxypropyl methyl cellulose, hydroxyethyl cellulose (e.g. available as Natrosol), iota carrageenan sodium carboxymethyl cellulose as well as synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g/ml. at 8% moisture) of 1.0.

Thickener, such as colloidal silica (e.g. the finely ground colloidal silica Syloid 244) is preferably also present in the dentifrice gel vehicle, in amount of about 0.1–10% by weight, most preferably about 5–10%.

When the oral composition is a dentifrice gel, it may be the entire composition or it may be present as a stripe in association with a separate portion of a dentifrice product.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a dentifrice will usually be in a collapsible tube, typically aluminum, lined lead or plastic, squeeze, pump or pressurized dispenser for metering out the contents, or in a tearable sachet, each having a label describing it, in substance, as a dentifrice.

Organic surface-active agents may be present in the oral compositions of the invention for increased prophylactic action, and to assist in achieving thorough and complete dispersion of the composition throughout the oral cavity. The organic surface-active agents are typically may be anionic, non-ionic or ampholytic in nature, and it is preferred to employ as the surface-active agent a detersive material which imparts to the composition detersive and foaming properties. Suitable types of such detergents are water-soluble higher fatty acid monoglyceride monosulfates, such as the sodium salts of the monosulfated monoglyceride hydrogenated coconut oil fatty acids, higher alkyl sulfates, such as sodium lauryl sulfate, alkyl aryl sulfonates, such as sodium dodecyl benzene sulfonate, olefin sulfonates, such as sodium olefin sulfate in which the olefin group contains 12 to 21 carbon atoms, higher alkyl sulfonacetates, higher fatty acid esters of 1,2-dihydroxy propane sulfonates, and substantially saturated higher aliphatic acyl amides of lower aliphatic amino carboxylic acid compounds, such as those having 12 to 16 carbons in the fatty acid, alkyl or acyl radicals. Examples of the last mentioned amides are N-lauroyl sarcosine, and the sodium, potassium, and ethanolamine salts of N-lauroyl, N-myristoyl or N-palmitoyl sarcosine which should be substantially free from soap or similar higher fatty acid material which tends to reduce substantially the effect of these compounds. The use of these sarcosine compounds in dentifrices of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of one mole of sorbitan monostearate with approximately 60 moles of ethylene oxide any condensates of ethylene oxide with propylene oxide condensates of propylene glycol ("Pluronics"-PLURONIC is a trade mark) or amphoteric agents such as quaternized imidazol derivatives which are available as "MIRANOL $C_2M$" (Miranol is a trademark) and betaines. It is preferred to use from 0.05% to 5% of the foregoing surface-active materials in the oral compositions.

Any suitable flavoring or sweetening materials may be employed in formulating a flavour for the oral compositions. Examples of suitable flavoring constituents include flavoring oils, e.g. oils of spearmint, peppermint, wintergreen, sassafras, clove, sage, eucalyptus, majoram, cinnamon, lemon and orange, as well as methylsalicylate. Suitable sweetening agents include sucrose, lactose, maltose, sorbitol, dipeptides, oxathiazin salts, perillartine and saccharine. Suitably, flavor and sweetening agents may together constitute from 0.01% to 5% or more of the dentifrice.

Various other adjuvant materials may be incorporated in the dentifrices of this invention. Examples are opacifying pigments if opacity is desired, preservatives, silicones, chlorophyll compounds, and ammoniated materials such as urea, diammonium phosphate and mixtures thereof. The adjuvants are incorporated in the dentifrices in amounts which do not substantially adversely affect the properties and characteristics desired. In particular, due to their propensity to form complexes with phytic compounds, compounds containing polyvalent cation are avoided.

In the description of the invention and the claims, amounts of ingredients employed within indicated general ranges are adjusted to provide a composition containing 100% by weight of all ingredients employed.

Although the invention is described with regard to the following illustrative examples, it will be apparent to one skilled in the art that various modifications may be made thereto which fall within its scope. All amounts expressed in parts are by weight unless otherwise indicated.

Example 1

Inhibition of Hydroxyapatite Formation by Sodium Phytate

The in vitro formation of HAP is measured titrimetrically via a pH stat procedure. Stock solutions of 0.1M $CaCl_2$ and 0.1M $NaH_2PO_4$ are prepared fresh in carbonate-free deionized distilled water. To 23 ml $CO_2$-free deionized distilled water 1.0 ml. of the stock phosphate solution and 1.0 ml. of an aqueous solution of $1 \times 10^{-4}M$ of the anticalculus agent being tested are added followed by 1.0 ml. of the stock calcium chloride solution which initiates the reaction. The reaction is conducted at pH 7.4 under a nitrogen atmosphere. Consumption of 0.1N NaOH is recorded automatically from which the time required for crystal formation is determined. Table 1 shows the results of this procedure.

TABLE 1

| Sodium Phytate Concentration | Time for HA Formation in Minutes | | |
|---|---|---|---|
| | In Water | Saliva* | In Phosphatases** |
| $1 \times 10^{-4}M$ | 218 | 116 | 38 |

\* = sodium phytate incubated in human saliva for 30 min. at R.T.
\*\* = sodium phytate incubated in enzymes for 30 minutes at 37° C.

The data shows that sodium phytate is an effective inhibitor of HAP formation in vitro, but when introduced in the oral environment, it is hydrolyzed to a substantial extent and loses efficacy with respect to HAP inhibition.

Example 2

Stabilization of Sodium Phytate Hydrolysis by Sodium Fluoride and/or Poly Carboxylate (Gantrez is Polyvinyl Methyl Ether/Maleic Anhydride)

Enzymatic hydrolysis is conducted in 100 millimolar morpholino-propane sulfonic acid-NaOH buffer solution (pH 7.0) containing 1.3 mg./ml. of the respective polyphosphate. Inhibitors of this invention are added (except to the control) to a final concentration of 1,000 ppm fluoride ion (from NaF) and 0.5% of the sodium salt of hydrolyzed methoxyethylene-maleic anhydride (1:1) copolymer, M.W. 70,000 (Gantrez S-97 Pharmaceutical Grade). Equal activities of acid, alkaline and inorganic pyrophosphatase are then added to yield a total phosphatase activity of 0.3 units/ml. Samples of each test solution are taken and total orthophosphate available in each sample measured after 3 hours hydrolysis in 4N HCl at 100° C. The reaction mixtures are incubated at 37° C. with shaking and aliquots taken at appropriate times through at least 90 minutes for orthophosphate determination. Table 1 shows the results expressed as percent phytate released due to hydrolysis of the polyphosphate.

TABLE 2

| Treatment | Percent Phytate lost after 4 hrs. |
|---|---|
| 3% Phytate + enzymes | 21.5 |
| 3% Phytate + enzymes + 0.24% NaF | None |
| 3% Phytate + enzymes + 0.24% NaF + 1% Gantrez | None |

Mixture contains 1 unit each of acid, alkaline phosphatases and pyrophosphatase; 0.2M MOPS buffer, 4mM $MgCl_2$ at pH 7.4 at 37° C. The data shows that the addition of NaF prevents the breakdown of phytate by the mixture of enzymes and that Gantrez polycarboxylate is not required to improve the inhibition effect.

Example 3

Anti-Calculus Efficacy of Sodium Phytate/NaF Composition

Thirty-six 20 day old male weanling Sprague-Dawley rats are randomized into three balanced groups. The animals are fed calculogenic diet (RC-12) and deionized water ad libitum during the entire study. Before initiation of the experimental treatments, all animals are inoculated with a suspension of S. mutans (6715) and A. Viscosus (OM2-105-NLY) to encourage plaque and calculus formation. The rats are treated once daily (excluding weekends) with 0.2 ml. of solution applied topically with an automatic pipettor. The experiment is conducted blind; the treatments are coded and unknown to the personnel involved in the study. The rats are sacrificed after 20 days treatment and the jaws are scored for the presence or absence of calculus.

TABLE 3

| Treatment | No. of Rats | Mean Calculus/ rat + S.D. | Diff. | Sig. |
|---|---|---|---|---|
| Distilled water | 12 | 78.3 ± 19.8 | — | — |
| 3.3% Pyrophosphate/ 0.24% NaF + 1% Gantrez - solution (positive control) | 12 | 48.7 ± 16.7 | −37.8 | 99% |
| 3.0% phytate (sodium salt) + 0.24% NaF | 12 | 14.0 ± 7.5 | −82 | 99% |

Total possible score/rat = 120

The data shows that a positive control (clinically proven effective composition in humans) is effective in reducing calculus formation in rats and that 3% phytate anion in the presence of 0.24% NaF is even more highly effective in reducing calculus formation in rats.

Example 4

(a) Dentifrice Gel Composition

| | Parts |
|---|---|
| Glycerine | 15.0 |
| PEG 600 | 5.0 |
| Iota Carrageenan | 0.6 |
| Phytate as sodium salt | 3-6 (phytate anion) |
| Sodium fluoride | 0.243 |
| Sylox 15 Silica Thickener | 7.00 |
| Amorphous silica polishing agent | 16.00 |
| Medium peppermint flavor | 1.15 |
| Sorbitol | 5.00 |
| SLS | 1.20 |
| Deionized water | Q.S. to 100 |

(b) Separate dentifrice gels as (a) above with sodium phytate replaced by each of:

Myo-inositol tetrakis (dihydrogen phosphate) sodium salts;

Myo-inositol trikis (dihydrogen phosphate) sodium salt;

Sodium phosphoglycerate; and

Sodium posphoenol pyruvate

Example 5

(a) Mouthrinse Composition

| | Parts |
|---|---|
| Sodium phytate | 1-3% (phytate ion) |
| Ethyl alcohol | 15 |
| Glycerine | 10 |
| Flavor | 0.4 |
| Sodium Fluoride | 0.01 to 0.05 |
| Pluronic F 108 | 2.0 |
| Deionized Water | Q.S to 100 |

(b) Separate mouthrinses as (a) above, with sodium phytate replaced by each of:

Myo-inositol tetrakis (dihydrogen phosphate) sodium salt;

Myo-inositol trikis (dihydrogen phytate) sodium salt;

Sodium phosphoglycerate; and

Sodium phosphoenol pyruvate

Example 6

Anticalculus Effect of Dentifrice

Dentifrices are tested in rats according to the protocol described in Example 3 above. The rats are treated intra-orally with 0.2 ml of the dentifrice slurries (1:1 with $H_2O$) once/day/5 days per wk.

| Treatment | No. of Rats | Mean Calculus/ rat ± S.D. | % Red | Sig. |
|---|---|---|---|---|
| Placebo dentifrice without sodium phytate | 12 | 57.3 ± 17.6 | — | — |
| 6% phytate anion + 0.24% NaF dentifrice | 12 | 31.3 ± 8.3 | 45.1 | 99% |
| 3% phytate anion + 0.24% NaF dentifrice | 12 | 38.2 ± 6.3 | 33.3 | 99% |

Compared to the placebo, the active dentifrices reduced calculus formaton significantly ($P < 0.01$). There were no significant differences among the active dentifrices.

Example 7

Anticaries Efficacy of Sodium Phytate +NaF

The anticaries efficacy of the combinations of sodium phytate plus NaF are evaluated after the topical intra-oral applications. The Weaning rats are kept on sucrose diet and inoculated with a caries producing Strep mutans. 100 microliters of solutions are applied topically on teeth 5 days/week twice daily. After 21 days application the rats are sacrificed and scored for caries (Tables) and for enamel solubility and fluoride uptake (Table 6).

TABLE 5

| Treatment | No. of Rats | Mean Fissure Caries/Rat | Smooth Surface Caries/Rat |
|---|---|---|---|
| Control, $H_2O$ | 11 | 6.4 | 14.2 |
| 300 ppm F/NaF | 11 | 3.5 | 6.8 |
| 300 ppm F/NaF + 1% Phytate Anion | 11 | 5.0 | 8.5 |
| 300 ppm F/NaF + 4% Phytate Anion | 11 | 5.2 | 8.8 |
| 600 ppm F/NaF | 11 | 2.3 | 3.9 |
| 600 ppm F/NaF + 1% Phytate Anion | 11 | 3.2 | 6.9 |
| 600 ppm F/NaF + 4% Phytate Anion | 11 | 1.9 | 4.7 |
| Least Sig. Diff. | | 2.3 | 3.8 |

Compared to the control, all sodium fluoride containing solutions significantly ($P < 0.05$) reduce fissure and smooth surface caries. The data indicates that 1 to 4% phytate does not interfere with the anticaries efficacy of NaF.

TABLE 6
Fluoride Uptake and Enamel Solubility Reductions with the Solution of NaF and NaF/Sodium Phytate

| Treatment | Enamel Solubility | % Reduction | Fluoride Uptake in Enamel |
|---|---|---|---|
| Control, Water | 157 | — | 51 |
| 300 ppm F/NaF | 122 | −22 | 359 |
| 300 ppm F/NaF + 1% Phytate Anion | 127 | −19 | 373 |
| 300 ppm F⁻ + 4% Phytate Anion | 126 | −20 | 339 |
| 600 ppm F/NaF | 116 | −26 | 531 |
| 600 ppm F/NaF + 1% Phytate Anion | 115 | −27 | 465 |
| 600 ppm F/NaF + 4% Phytate Anion | 120 | −24 | 427 |
| Least Sig. Diff. at (P<0.05) | 13.3 | | 95.0 |

The number of rats subjected to each treatment in Table 6 is the same as in Table 5 (11 in each group).

The data shows that fluoride (300 to 600 ppm F/NaF) is effective in reducing the solubility of enamel after an acid challenge and the presence of phytate does not significantly impair the activity of fluoride. Additionally, the addition of phytate with sodium fluoride has no significant effect on fluoride uptake in enamel since there are no significant differences between NaF alone and NaF/Phytate combinations for the fluoride contents in enamel.

Collectively, the results in Examples 1-3, 6 and 7 show that fluoride/phytate combination is effective against calculus and caries formation in vitro and in vivo and the addition of phytate with sodium fluoride does not adversely affect the anticaries efficacy of fluoride.

The invention has been described with respect to certain preferred embodiments and it will be understood that modifications and variations thereof obvious to those skilled in the art are to be included within the purview of this application and the scope of the appended claims.

We claim:

1. An anticalculus oral composition consisting essentially of a dentally acceptable oral vehicle and homogeneously distributed therein about 0.1-7% by weight of a compound having C—O—P bonds selected from the group consisting of phytic acid, myo-inositol tetrakis dihydrogen phosphate, myo-inositol trikis dihydrogen phosphate, phosphoglyceric acid, phosphoenol pyruvic acid and alkali metal salt thereof as inhibitor of hydroxyapatite formation and about 0.02-2.2% by weight of an alkali metal fluoride as inhibitor of enzymatic hydrolysis and also anti-caries agent, said alkali metal fluoride being the sole anti-caries agent which provides fluoride to the oral composition, said oral composition containing no compounds which provide polyvalent cations capable of forming a complex with said inhibitor of hydroxyapatite formation.

2. The anticalculus oral composition claimed in claim 1 wherein said compound having C—O—P bonds is phytic acid or an alkali metal salt thereof.

3. The anticalculus oral composition claimed in claim 1 wherein said alkali metal fluoride is sodium fluoride.

4. The anticalculus oral composition claimed in claim 2 wherein said alkali metal fluoride is sodium fluoride.

5. The anticalculus oral composition claimed in claim 1 wherein said dentally acceptable oral vehicle contains water and humectant collectively in amount of about 10-90% by weight and about 5-50% by weight of a siliceous polishing agent.

6. The anticalculus oral composition claimed in claim 5 wherein said compound having C—O—P bonds is phytic acid or the sodium salt thereof and said alkali metal fluoride is sodium fluoride.

7. The anticalculus oral composition claimed in claim 1 wherein said dentally acceptable oral vehicle contains about 70-99.99% by weight of water-non-toxic alcohol mixture and the weight ratio of water to non-toxic alcohol is from about 1:1 to about 20:1.

8. The anticalculus oral composition claimed in claim 7 wherein said compound having C—O—P bonds is phytic acid or the sodium salt thereof, said alkali metal fluoride is sodium fluoride and said non-toxic alcohol is ethyl alcohol.

9. A method of inhibiting dental calculus comprising applying to teeth a calculus-inhibiting amount of an anticalculus oral composition having a pH of about 4.5 to about 9 consisting essentially of a dentally acceptable oral vehicle and homogeneously distributed therein about 0.1-7% by weight of a compound having C—O—P bonds selected from the group consisting of phytic acid myo-inositol tetrakis (dihydrogen phosphate), myo-inositol trikis (dihydrogen phosphate), phosphoglyceric acid, phosphenol pyruvic acid and alkali metal salt thereof as inhibitor of enzymatic hydrolysis and also anti-caries agent, said alkali metal fluoride being the sole anti-caries agent which provides fluoride to the oral composition, said oral composition containing no compounds which provide polyvalent cations capable of forming a complex with said inhibitor of hydroxyapatite formation, said composition when being so applied being effective to inhibit dental calculus.

* * * * *